United States Patent
Farrokhnia et al.

(10) Patent No.: US 6,231,231 B1
(45) Date of Patent: May 15, 2001

(54) MODULAR INTERCHANGEABLE PHANTOMS FOR MULTIPLE X-RAY SYSTEMS

(75) Inventors: Farshid Farrokhnia, Brookfield; Kenneth Scott Kump, Waukesha; Donald G. Webster, Oconomowoc, all of WI (US); Richard Aufrichtig, Mountain View, CA (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/339,653

(22) Filed: Jun. 24, 1999

(51) Int. Cl.[7] .................................................... G01D 18/00
(52) U.S. Cl. ........................................... 378/207; 378/204
(58) Field of Search ........................... 378/18, 204, 207; 250/252.1

(56) References Cited

U.S. PATENT DOCUMENTS

| | | |
|---|---|---|
| 4,126,789 | 11/1978 | Vogl et al. . |
| 4,649,561 * | 3/1987 | Arnold ................................ 378/207 |
| 5,056,130 * | 10/1991 | Engel .................................. 378/207 |
| 5,095,499 | 3/1992 | Wentz . |
| 5,164,978 * | 11/1992 | Goodenough et al. ............. 378/207 |
| 5,191,621 | 3/1993 | Brok . |
| 5,276,726 | 1/1994 | Galkin . |
| 5,416,816 | 5/1995 | Wenstrup et al. . |
| 5,481,587 | 1/1996 | Mazess . |
| 5,511,107 | 4/1996 | Sliski . |
| 5,539,799 | 7/1996 | Schulze-Ganzlin et al. . |
| 5,544,238 | 8/1996 | Galkin . |
| 5,651,046 | 7/1997 | Floyd et al. . |
| 5,841,835 | 11/1998 | Auffichtig et al. . |

OTHER PUBLICATIONS

J.L. Poletti, *Performance Assessment of CT Scanners*, Australasia Physical & Engineering Sciences in Medicine (1986) vol. 9 No. 4, pp. 168–172.

* cited by examiner

Primary Examiner—David P. Porta
(74) Attorney, Agent, or Firm—McAndrews, Held & Malloy, Ltd.

(57) ABSTRACT

Modular interchangeable phantoms for multiple x-ray systems are provided. A variety of x-ray phantoms may be interchangeably inserted into a modular phantom carrier. Once a phantom has been inserted into the carrier, the phantom is locked to the carrier by either at least one rotating fastener or a plastic ring with at least one fastening pin. The carrier is then inserted into an x-ray system and x-rays are transmitted through the phantom. The phantom carrier also includes an interior mesh allowing measurement of the resolution non-uniformity of the x-ray system. Three phantoms for use with the modular phantom carrier are presented. Each phantom includes a number of sub-phantoms useful in the determination of various parameters of the x-ray system. These sub-phantoms include a step-intensity sub-phantom for measuring the dynamic range and linearity of the x-ray system, a contrast detail sub-phantom for measuring the contrast of the x-ray system, a mesh sub-phantom for measuring the resolution non-uniformity of the x-ray system, and a resolution sub-phantom and a coupon sub-phantom both for measuring the Modulation Transfer Function (MTF) of the x-ray system. The phantoms also preferably include a lead perimeter ring attached near the perimeter of each phantom to aid in the orientation and positioning of the phantom as well as lead line segments or fiducials separating or outlining various sub-phantoms.

46 Claims, 11 Drawing Sheets

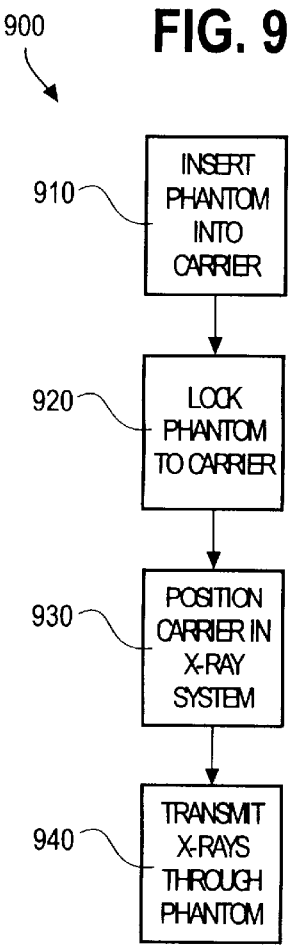
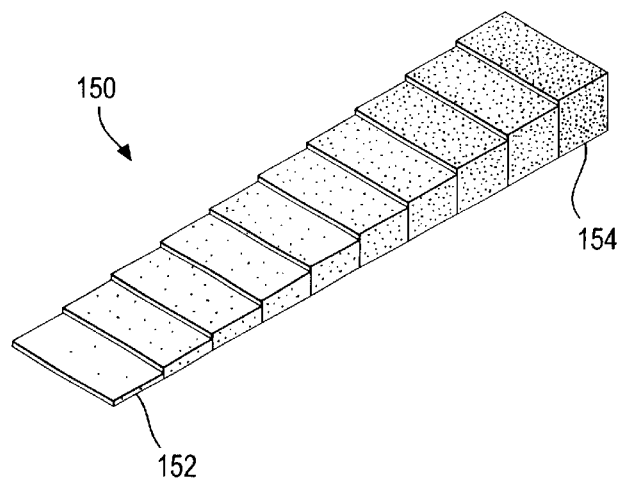
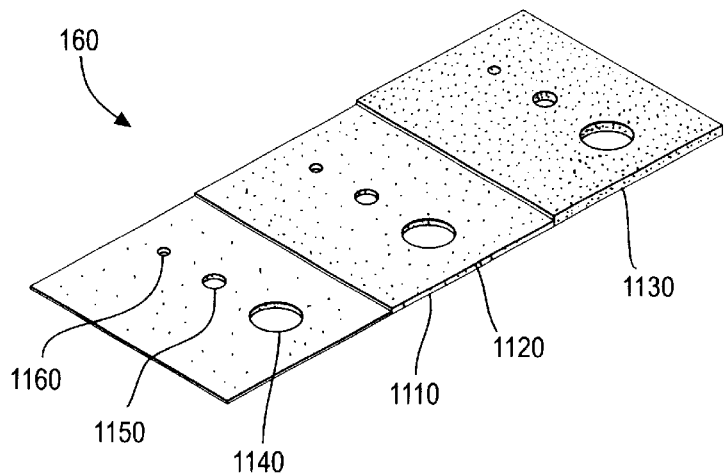

MODULAR INTERCHANGEABLE PHANTOMS FOR MULTIPLE X-RAY SYSTEMS

BACKGROUND OF THE INVENTION

The present invention generally relates to a modular x-ray phantom system. More particularly, the present invention relates to a modular x-ray phantom system comprising a plurality of interchangeable phantoms and a modular phantom carrier.

X-ray systems, such as an image intensifier, storage phosphor plates or digital detectors, typically include an x-ray emitter and an x-ray receiver. A target to be viewed, such as a human body, is arranged between the x-ray emitter and the x-ray receiver. X-rays produced by the emitter travel through the target to reach the receiver. As the x-rays travel from the emitter through the target, internal components of the target may decrease the energy of the x-rays to varying degrees through effects such as the blocking or absorption of some of the x-rays. The blocking or absorption of x-rays within the target causes the received x-ray energy levels to vary. The x-ray receiver receives the x-rays which have traveled through the target. An image of the target is generated at the x-ray receiver. The image produced at the receiver contains regions of light and dark which correspond to the varying intensity levels of the x-rays which have passed through the target.

The x-ray images may be used for many purposes. For instance, internal defects in the target may be detected. Additionally, changes in internal structure or alignment may be determined. Furthermore, the image may show the presence or absence of objects in the target. The information gained from x-ray imaging has applications in many fields, including medicine and manufacturing.

In order to help ensure that x-ray images may be used reliably, it is advantageous to calibrate x-ray systems. The calibration of x-ray systems is important for several reasons, including image quality. Poor image quality may prevent reliable analysis of the x-ray image. For example, a decrease in image contrast quality may yield an unreliable image that is not usable. Additionally, the advent of real-time imaging systems has increased the importance of generating clear, high quality images. The calibration of x-ray systems may help to produce a distinct and usable representation of the target.

The calibration of x-ray systems is also important for safety reasons. For example, exposure to high levels of x-ray energy may involve some health risk to humans. Because of the health risk, governmental standards are set for the use of x-ray systems. The level of x-ray energy emitted by an x-ray system may be measured in terms of radiation dosage. Calibration of x-ray systems may ensure that the radiation dosage to which the target is exposed does not exceed regulatory standards.

One device that may be used in the calibration of x-ray system parameters, such as image quality and radiation dosage, is an x-ray phantom. Several types of phantoms exist, including physical replica phantoms and physics-based phantoms. For example, a physical replica phantom may be a physical replica of an x-ray target, such as a human body part. A physics-based phantom may be comprised of various structures affixed to a common base. The structures of a physics-based phantom may possess varying characteristics, such as shape, size, density, and composition. Furthermore, the structures of physics-based phantoms may be constructed from various materials, including metal and plastic.

The structures of physics-based phantoms may affect the intensity of the x-rays which pass through the physics-based phantom. For example, metal structures may block some or most of the x-rays. Additionally, plastic structures may merely provide minimal attenuation of the x-rays. A pattern resulting from the changes in the intensity of received x-rays is represented in an x-ray image. The resulting pattern in the x-ray image may be easy to detect and analyze due to factors such as the contrast produced by the difference in received x-ray intensities.

Currently known phantoms may serve a variety of purposes. For example, phantoms may test performance parameters of the x-ray system. Also, phantoms, combined with radiation probes, may be used to gauge the radiation dosage of x-ray energy emitted by the emitter. Furthermore, phantoms may be used for calibration and image quality assessment.

Typically, physics-based phantoms may be designed to measure one or more parameters of an x-ray system. Different phantoms may produce different patterns of x-ray intensity or attenuation. The different patterns of x-ray intensity or attenuation may be used to measure or test different performance parameters of the x-ray system. Thus, multiple phantoms may be necessary to measure a plurality of x-ray system parameters.

However, the use of multiple phantoms in an x-ray system may introduce unwanted variance in x-ray system calibration. For instance, the use of multiple phantoms in an x-ray system may introduce variance in the positioning of the phantom as a result of factors such as variation in phantom size and configuration. Variation in the positioning of the phantom may yield variation in the x-ray image. Variation in the x-ray image may result in loss of accuracy in x-ray system calibration. However, positioning of the phantom in a consistent location in the x-ray field may assist in reliable and consistent measurement of parameters, such as image quality and radiation dosage, on x-ray systems.

Consistent positioning of the phantom also may assist in providing trending data for x-ray system parameters. Trending is known as the comparison of x-ray system parameters over time to establish a trend of x-ray system parameters. Tracking of trending may be important to evaluate the performance of the x-ray system over time.

Often, a phantom carrier is used to position a phantom in an x-ray system. As previously mentioned, each x-ray system has an x-ray receiver. The x-ray receiver has an aperture through which the x-rays are received. The characteristics of the aperture, such as size, may vary depending upon the x-ray system being used. A modern phantom carrier comprises an x-ray phantom embedded in a frame. The phantom carrier serves to position the phantom in the path of the x-ray energy received through the aperture.

Due to the variance in the characteristics of apertures (such as size) in different x-ray systems, a phantom carrier may be specific to the aperture of the particular x-ray system. Thus, to provide calibration of x-ray systems with different apertures, a plurality of phantom carriers may be required.

A physics-based phantom carrier is described in U.S. Pat. No. 5,841,835 issued to Aufrichtig et al. ("Aufrichtig"). The phantom embedded in the Aufrichtig phantom carrier may be used in the calibration and standardization of digital x-ray fluoroscopy and radiography systems. The Aufrichtig phantom carrier positions the embedded phantom in the path of the x-ray beam. The Aufrichtig phantom carrier is a single piece, integrated phantom carrier with an embedded phantom.

Characterizing the performance of an x-ray system may require multiple phantoms embedded in multiple carriers to measure differing x-ray system parameters. Currently, the use of multiple phantom carriers in an x-ray system may introduce problems, such as variance in positioning, similar to those discussed above with the use of multiple phantoms. Variance in phantom carrier design or positioning may introduce spatial variation in measurement and trending of x-ray system parameters.

Additionally, the manufacture of multiple phantom carriers may be very labor intensive due to factors such as variation in design and customization. The manufacture of multiple phantom carriers may also be expensive due to factors such as material cost and production time. The multiple integrated phantom systems may also require a large amount of storage space.

Thus, a need has long existed for an x-ray phantom system that may be transferred easily between a plurality of x-ray systems. A need exists for an x-ray phantom system which may allow a phantom to be repeatedly positioned within an x-ray system with minimal spatial variance, thus increasing the accuracy of x-ray system calibration. Additionally, a need exists for an x-ray phantom system which may allow a plurality of phantoms to be repeatedly and reliably positioned in an x-ray system. A need also exists for an x-ray phantom system which may allow a phantom to be easily transferred among a plurality of x-ray systems with different apertures. In addition, a need exists for an x-ray phantom which may allow more accurate calibration of x-ray systems and may allow measurement of additional parameters.

SUMMARY OF THE INVENTION

A preferred embodiment of the present invention provides modular interchangeable phantoms for multiple x-ray systems. A variety of x-ray phantoms may be interchangeably inserted into a modular phantom carrier. Once a phantom has been inserted into the carrier, the phantom is locked to the carrier and then inserted into an x-ray system wherein x-rays are transmitted through the phantom. Multiple phantoms that may be interchanged in the modular phantom carrier are presented according to alternative embodiments of the present invention. Each phantom includes a number of sub-phantoms useful in the determination of various parameters of the x-ray system including a step-intensity sub-phantom for measuring the dynamic range and linearity, a contrast detail sub-phantom for measuring the contrast, a mesh sub-phantom for measuring the resolution non-uniformity, and a resolution sub-phantom and a coupon sub-phantom both for measuring the Modulation Transfer Function (MTF). The phantoms also preferably include a lead perimeter ring to aid in the orientation and positioning of the phantom as well as lead line segments or fiducials separating or outlining various sub-phantoms.

The phantoms of the modular phantom carrier system may be easily transferred between any number of x-ray systems. The modular phantom carrier allows any of a number of inserted phantoms to be repeatedly and accurately positioned within an x-ray system. Additionally, the improved phantoms allow the measurement of additional parameters of an x-ray system and may offer more accurate calibration of x-ray systems.

These and other features of the present invention are discussed or apparent in the following detailed description of the preferred embodiments of the invention.

BRIEF DESCRIPTION OF THE DRAWINGS

FIG. 9 illustrates a flowchart for using the modular phantom carrier according to a preferred embodiment of the present invention.

FIG. 10 illustrates a preferred embodiment of the step intensity sub-phantom according to the present invention.

FIG. 11 illustrates a preferred embodiment of the contrast detail sub-phantom according to the present invention.

DETAILED DESCRIPTION OF THE PREFERRED EMBODIMENTS

Figure 1:
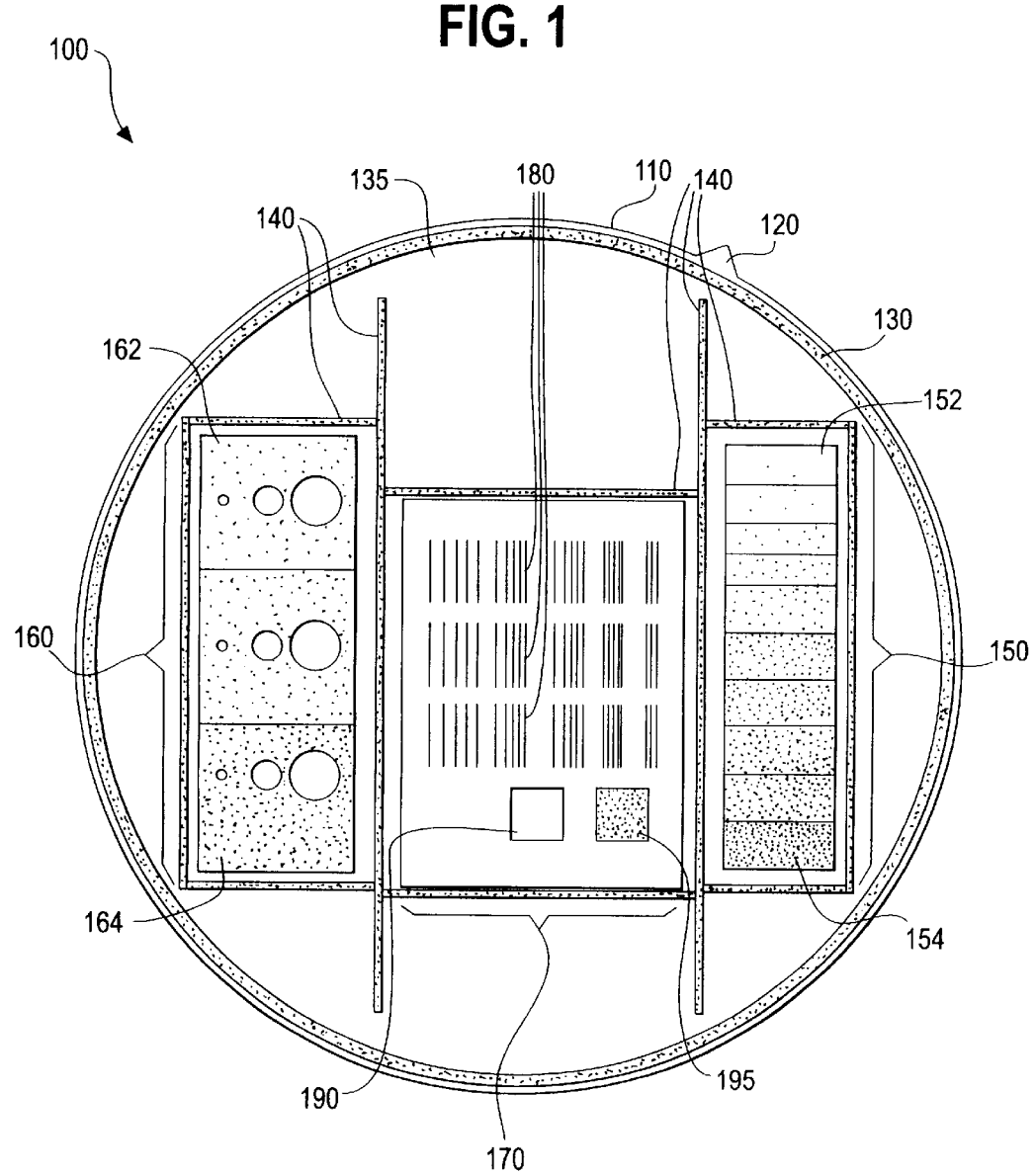
FIG. 1 illustrates a preferred embodiment of an x-ray phantom according to the present invention.

FIG. 1 illustrates a preferred embodiment of an x-ray phantom 100 of the present invention. The phantom 100 includes a base 110, a positioning tab 120, a perimeter ring 130, an open area 135, line segments 140, a step intensity sub-phantom 150, a contrast detail sub-phantom 160, and a resolution sub-phantom 170. The resolution sub-phantom 170 includes resolution patterns 180, a high intensity contrast region 190 and a low intensity contrast region 195.

The positioning tab 120 extends radially from the base 110. The positioning tab 120 is used to assure that the phantom 100 is positioned correctly inside a carrier, as will be detailed below. The positioning tab 120 minimizes rotational motion of the phantom 100 and also prevents the phantom 100 from being placed in a carrier incorrectly, for example upside down. Additional positioning tabs may be added to the x-ray phantom to further minimize the motion of the phantom.

The perimeter ring 130, line segments 140, step intensity sub-phantom 150, contrast detail sub-phantom 160, and resolution sub-phantom 180 are affixed to the top of the base 110. The perimeter ring 130 runs along the perimeter of the base 110. The line segments 140 separate the step intensity sub-phantom 150, contrast detail sub-phantom 160, and resolution sub-phantom 170 from each other and from the open area 135.

In operation, the phantom 100 may be inserted into an x-ray system (not shown). In an x-ray system, x-rays are emitted by an emitter, pass through the phantom 100, and are received by a receiver. The differing sub-phantoms comprising the phantom 100 attenuate x-rays incident on the sub-phantoms by differing amounts and may be influenced by the composition or structure of the sub-phantom, for example. The x-ray attenuation provided by the sub-phantoms results in spatially varying x-ray intensity at the receiver. The spatially varying intensities may be received at the receiver and displayed and analyzed to determine the performance parameters of the x-ray system. Each sub-phantom may measure a different performance parameter or set of performance parameters of the x-ray system.

The perimeter ring 130 and the line segments 140 are preferably composed of a metallic layer such as lead, for example, that blocks much of the x-ray transmission through the phantom 100. Because the perimeter ring 130 and the line segments 140 block a comparatively large amount of the x-ray transmission through the phantom, they are easily detectable when displayed and analyzed. The perimeter ring 130 and line segments 140 thus provide easily seen "landmarks." These landmarks aid in determining the orientation and positioning of the phantom 100. For example, the perimeter ring 130 may be used to define the perimeter of the phantom 100 in an x-ray image to aid in recognition and interpretation of phantom data. Additionally, the line segments 140 may be used to separate the sub-phantoms 150–170 and also to define the perimeters of each sub-phantom.

FIG. 10 illustrates a preferred embodiment of the step intensity sub-phantom 150 according to the present invention. The step intensity sub-phantom 150 is preferably composed of a metallic layer such as copper, for example. The step intensity sub-phantom 150 preferably includes ten regions, each region composed of a differing thickness of the copper layer. The thickness of the copper layer in each region ranges from a thinnest region 152 to a thickest region 154. Because the intensity of the x-rays penetrating a given region is inversely proportional to the thickness of the region, each region provides a level or "step" in intensity from greatest intensity to least intensity. Preferably, each of the regions of the step intensity sub-phantom 150 are approximately 20 mm across by 7.5 mm high and range linearly from about 0.25 mm to 2.5 mm in thickness. The step intensity sub-phantom 150 may be used to determine the dynamic range and the linearity of the x-ray system. Although the preferred embodiment of the step intensity sub-phantom 150 is comprised of ten regions, a greater or lesser number of regions of varying sizes and thickenesses may also be used.

FIG. 11 illustrates a preferred embodiment of the contrast detail sub-phantom 160 according to the present invention. The contrast detail sub-phantom 160 is preferably composed of a metallic layer such as aluminum, for example. The contrast-detail sub-phantom 160 preferably includes three regions 1110–1130, each region composed of a differing thickness of the aluminum layer. The thickness of the aluminum ranges from a thinnest layer 1110 to a thickest layer 1130. Each region preferably contains three apertures 1140–1160 of approximately 7.6 mm, 3.8 mm. and 1.9 mm in diameter. Preferably, each of the regions 1110–1130 of the contrast detail sub-phantom 160 are approximately 30 mm across by 20 mm high with thicknesses of 1 mm, 2 mm, and 3 mm. The contrast detail sub-phantom 160 may be used to determine the relative contrast and contrast-to-noise ratio of the x-ray system. Although the preferred embodiment of the contrast detail sub-phantom 160 is comprised of three regions 1110–1130 with three apertures 1140–1160 per region, a greater or lesser number of regions and apertures per region may also be used.

Figure 12:
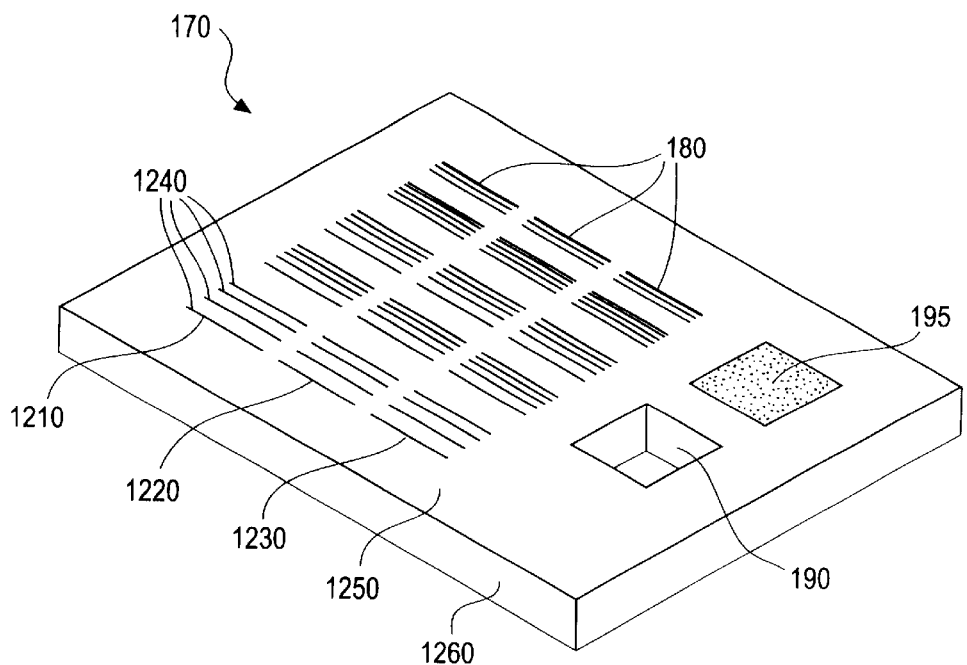
FIG. 12 illustrates a preferred embodiment of the resolution sub-phantom according to the present invention.

FIG. 12 illustrates a preferred embodiment of the resolution sub-phantom 170 according to the present invention. The resolution sub-phantom 170 is preferably composed of a thin metallic layer 1250 such as lead foil, for example on top of a base 1260 such as plastic, for example. The resolution sub-phantom 170 and the metallic layer 1250 have a uniform thickness throughout. The resolution sub-phantom 170 preferably includes fifteen resolution patterns 180 arranged in three rows 1210–1230, each row 1210–1230 including five resolution patterns 180. Each resolution pattern 180 is preferably formed by five slit-like apertures 1240 extending through the metallic layer 1250. In each resolution pattern 180, the width of the five slit-like apertures 1240 as well as the spacing between apertures 1240 may be varied. The resolution sub-phantom 170 may be used to determine the Modulation Transfer Function (MTF) of the x-ray system.

Although the preferred embodiment of the resolution sub-phantom 170 includes fifteen resolution patterns 180 arranged in three rows 1210–1230 of five resolution patterns per row 1210–1230, a greater or lesser number of resolution patterns may also be used. Additionally, the configuration of the resolution patterns 180 into rows 1210–1230 or other structures may be altered. Additionally, the widths and lengths of the apertures 1240 of the resolution patterns 180 may be varied.

The high intensity contrast region 190 is preferably comprised of a an aperture in the metallic layer 1250 and the base 1260. The low intensity contrast region 195 is preferably comprised of a thick metallic tag such as a lead block. The high intensity contrast region 190 and the low intensity contrast region 195 provide high and low contrast regions respectively, and may be used for image normalization.

Figure 2:
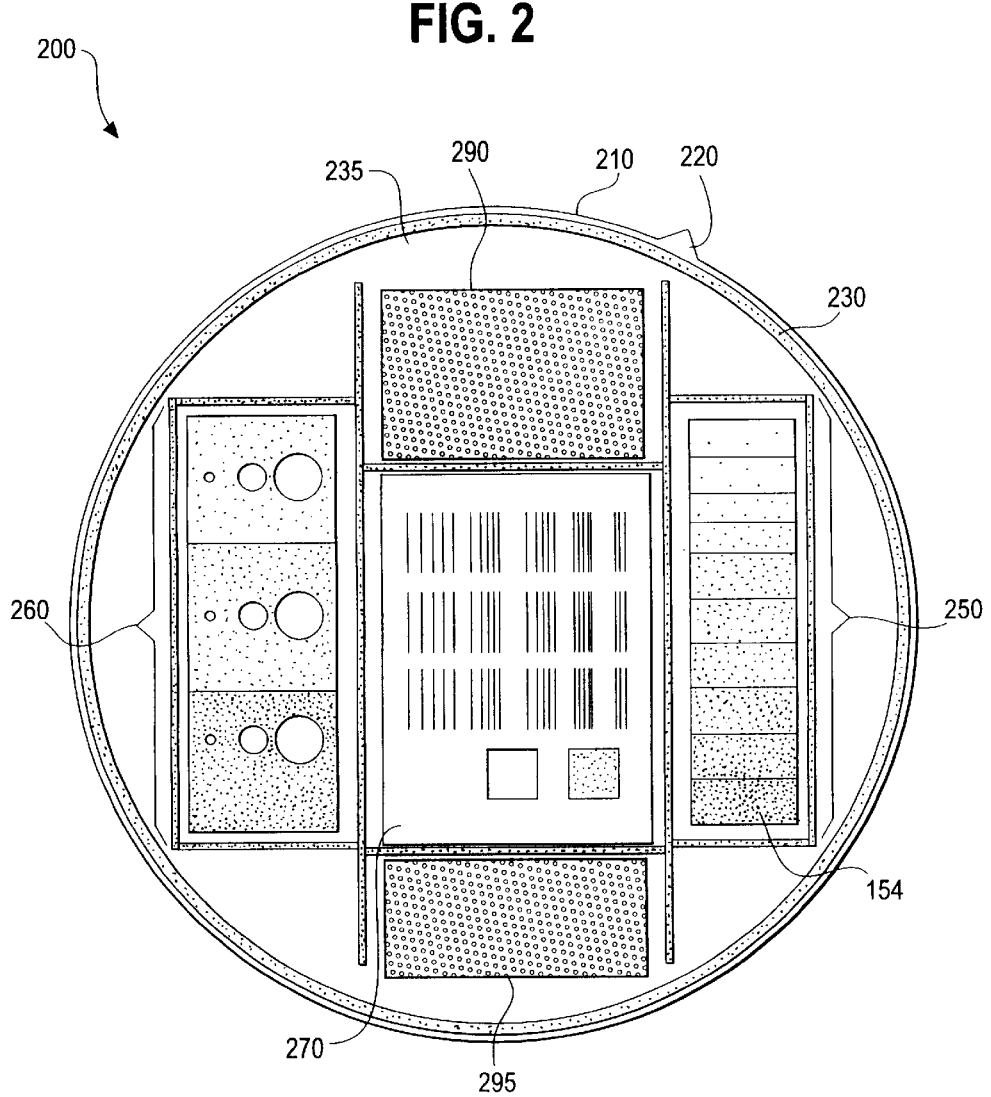
FIG. 2 illustrates an alternative preferred embodiment of an x-ray phantom with mesh areas according to the present invention.

FIG. 2 illustrates an alternative preferred embodiment of an x-ray phantom 200 with mesh areas of the present invention. The mesh phantom 200 includes the base 210, positioning tab 220, perimeter ring 230, open area 235, line segments 240, step intensity sub-phantom 250, contrast detail sub-phantom 260, and resolution sub-phantom 270. The mesh phantom 200 additionally includes an upper mesh 290 and a lower mesh 295. The mesh phantom 200 is generally similar to the phantom 100 of FIG. 1 with the addition of the upper mesh 290 and the lower mesh 295.

Figure 13:
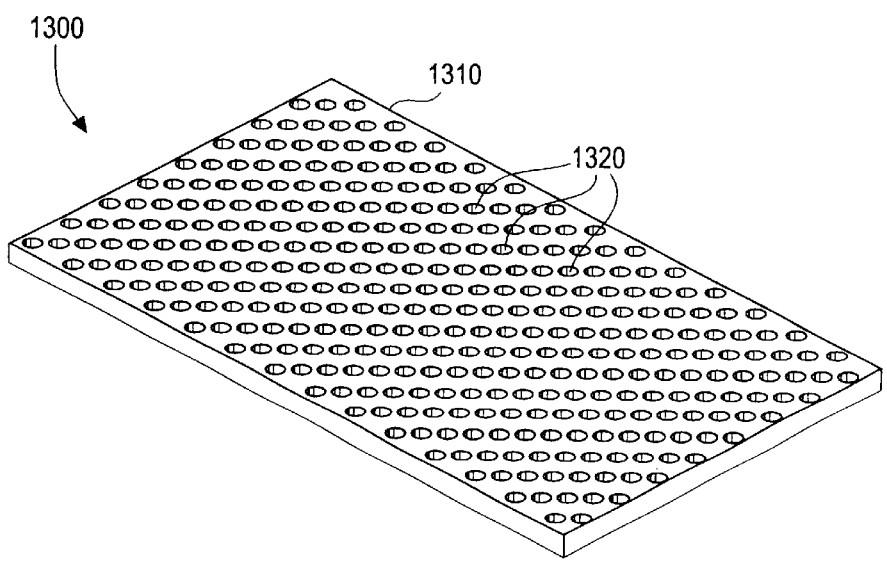
FIG. 13 illustrates a preferred embodiment of a mesh area similar to the upper mesh and lower mesh according to the present invention.

FIG. 13 illustrates a preferred embodiment of a mesh area 1300 similar to the upper mesh 290 and lower mesh 295 according to the present invention. The mesh area 1300 is preferably a metallic mesh such as steel meshes. The mesh area 1300 includes a metallic strip 1310 having a number of regularly spaced apertures 1320. The upper mesh 290 and lower mesh 295 may be used to determine the resolution non-uniformity of the x-ray system. The resolution non-uniformity of the x-ray system may be determined across a single mesh or may be determined across multiple meshes and then compared. Comparison of the resolution non-uniformity among multiple meshes may allow a determination of resolution non-uniformity across a greater area and thus may be more accurate of the resolution non-uniformity of an x-ray system as a whole. Thus, although the preferred embodiment of the mesh phantom 200 includes two meshes to provide increased accuracy in determining system non-uniformity, a single mesh may be used. Additionally, more than two meshes may be used to yield an even more accurate indication of system non-uniformity. The sizes, thicknesses, and spacing of the apertures of the meshes may also be varied.

Figure 3:
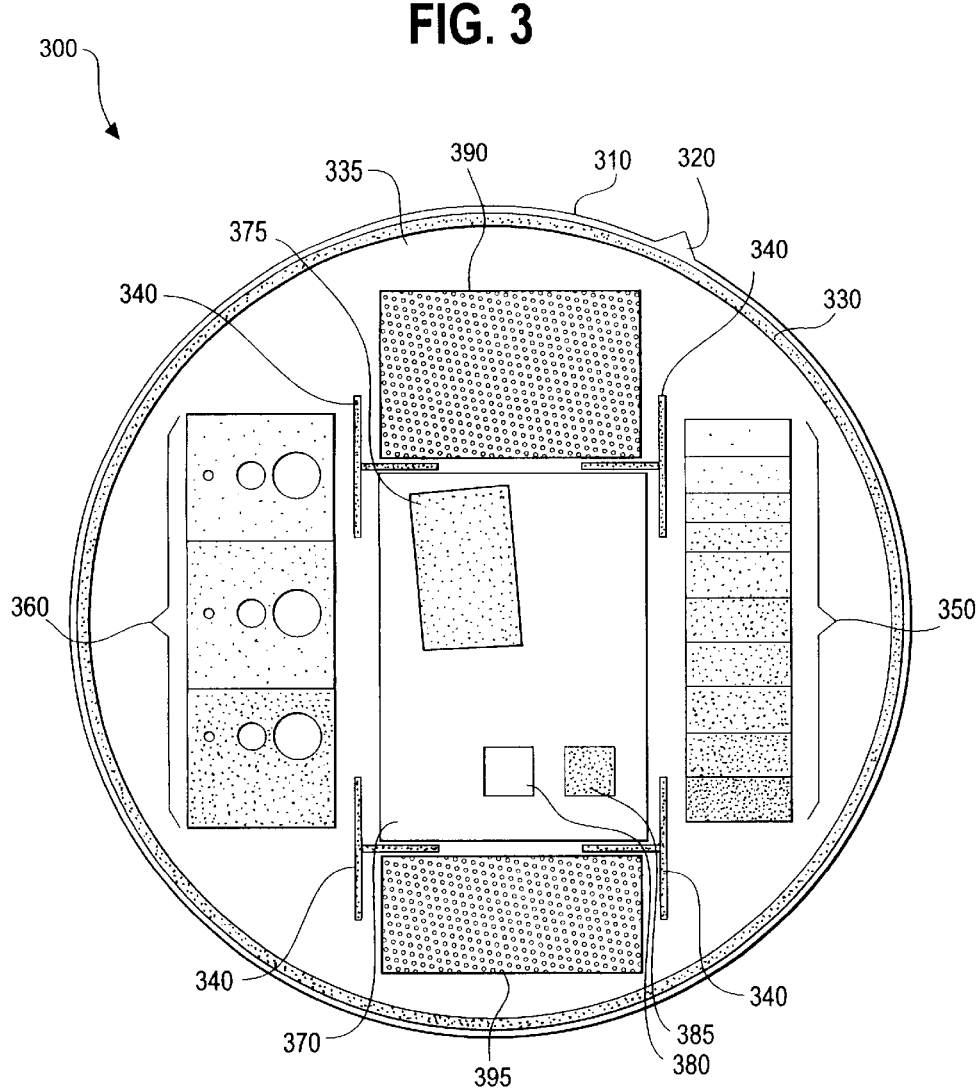
FIG. 3 illustrates an alternative preferred embodiment of a x-ray phantom with a coupon sub-phantom according to the present invention.

FIG. 3 illustrates an alternative preferred embodiment of a x-ray phantom 300 with a coupon sub-phantom 370 of the present invention. The coupon phantom 300 includes the base 310, positioning tab 320, perimeter ring 330, open area 335, step intensity sub-phantom 350, and contrast detail sub-phantom 360 similar to the phantom 100 of FIG. 1 and mesh phantom 200 of FIG. 2. Additionally the coupon phantom 300 includes an upper mesh 390 and a lower mesh 395 similar to the mesh phantom 200 of FIG. 2. However, the coupon phantom 300 includes fiducials 340 instead of the line segments 140 of the phantom 100 of FIG. 1. Additionally, the coupon phantom 300 includes a coupon sub-phantom 370 instead of the resolution sub-phantom 170 of FIG. 1.

Figure 14:
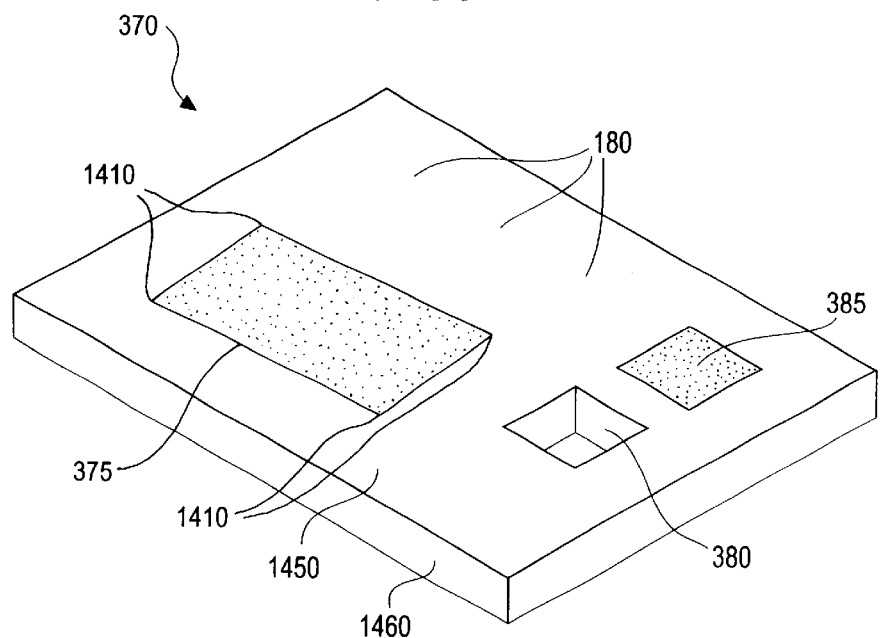
FIG. 14 illustrates a preferred embodiment of the coupon sub-phantom according to the present invention.

FIG. 14 illustrates a preferred embodiment of the coupon sub-phantom 370 according to the present invention. The coupon sub-phantom 370 includes a coupon 375 in addition to a thin metallic layer 1450 such as lead foil, for example, on top of a base 1460 such as plastic, for example, a high intensity contrast region 380 and a low intensity contrast region 385 similar to the phantom 100 of FIG. 1. The coupon sub-phantom 370 and the metallic layer 1450 have a uniform thickness throughout. The coupon 375 is preferably composed of a metallic sheet such as a tungsten sheet, for example. Similar to the resolution patterns 180 of the resolution sub-phantom 170 of FIG. 1, the coupon 375 may be used to determine Modulation Transfer Function (MTF) of the x-ray system. Although the preferred embodiment of the coupon phantom 300 includes one coupon 375, a greater number of coupons of varying sizes and thickenesses may also be used.

The coupon 375 has coupon edges 1410. The MTF of the X-ray system may be determined by comparing the transitions at the coupon edges 1410 with respect to position. Examining the resolution patterns 180 of the resolution sub phantom 170 of FIG. 1, the resolution patterns 180 vary only in horizontal aspect, no variation is seen vertically. Thus, the resolution patterns 180 may only calculate the horizontal MTF of the system and not the vertical MTF of the system.

However, in the coupon sub-phantom 370, the coupon edges 1410 have been rotated 5 degrees with respect to the coupon sub-phantom 370. The coupon edges 1410 thus provides both vertical and horizontal variation, The horizontal and vertical variation allow the computation of both the horizontal MTF and vertical MTF of the x-ray system. The amount of rotation of the coupon 375 is related to the resolution of the x-ray system in terms of pixel size as well as the size of the coupon 375. Additionally, rotating the coupon 375 assists in the measurement of the MTF because the edges of the coupon 375 do not align with a pixel column. For many commercially available systems, a rotation of approximately 5 degrees may be the most desired rotation although other rotations may also provide accurate MTF determination.

The fiducials 340 of the coupon phantom 300 of FIG. 3 are preferably composed of a metal such as lead for example. The fiducials 340 are generally similar in operation to the line segments 140 of the phantom 100 of FIG. 1. That is, the fiducials 340 are easily seen "landmarks" in an x-ray image of the phantom. The fiducials 340 may thus aid in determining the orientation and positioning of the coupon phantom 300 as well as aid in separating and locating the various sub-phantoms.

The shape, size, and positioning of the fiducials 340 may also be used to distinguish between phantoms. For example, a phantom measuring parameters A and B may have a different shape, size and orientation of fiducials than a phantom measuring parameters B and C. For example, the phantom 100 of FIG. 1 may be distinguished from the coupon phantom 300 of FIG. 3 because the fiducials 340 differ from the line segments 140. Distinguishing between phantoms on the basis of fiducials is useful because the fiducials are made of lead and thus are easily seen in x-ray images.

Figure 4:
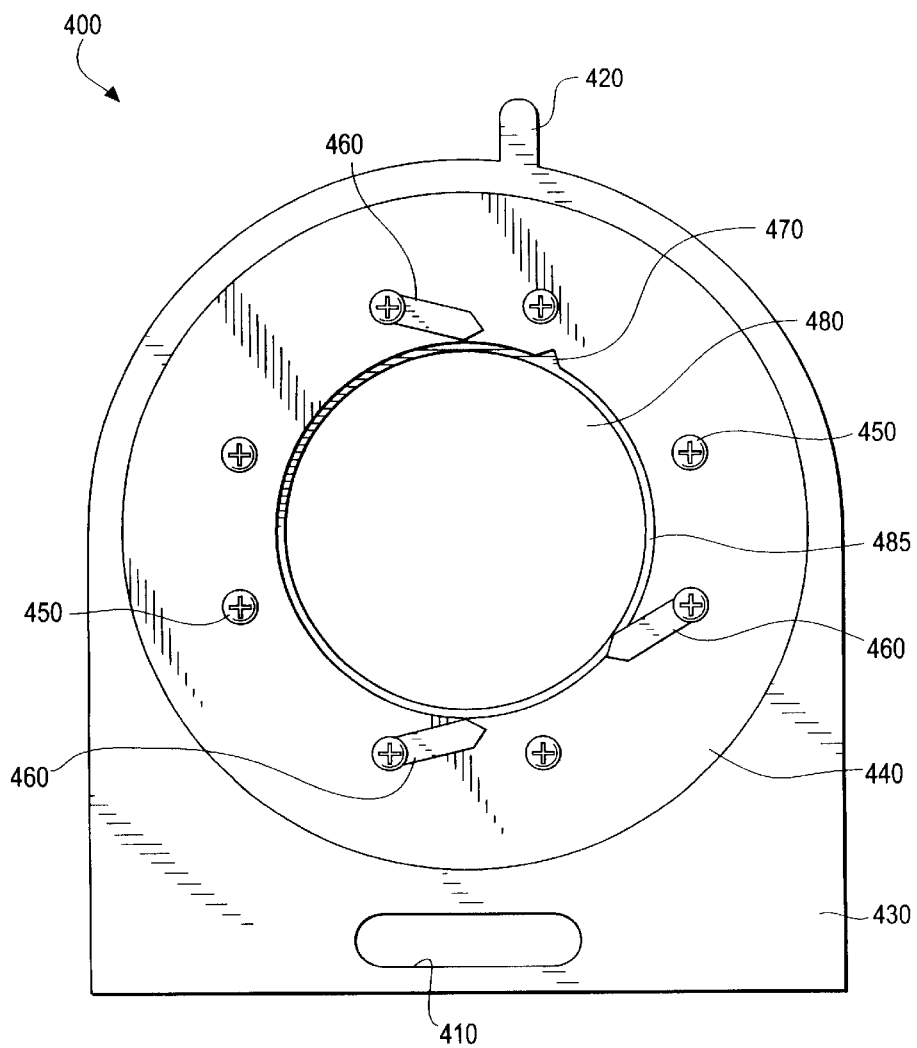
FIG. 4 illustrates a preferred embodiment of the modular phantom carrier according to the present invention.

FIG. 4 illustrates a preferred embodiment of a modular phantom carrier 400 according to the present invention. The modular phantom carrier 400 includes a handle 410, an alignment pin 420, an exterior frame 430, an interior mesh 440, a plurality of casing fasteners 450, a plurality of rotating fasteners 460, a positioning notch 470, and a phantom insert aperture 480.

The exterior frame 430 of the modular phantom carrier 400 is preferably composed of a sturdy, metallic frame such as an aluminum frame. The exterior frame 430 is generally flat and planar. The exterior frame 430 includes a handle 410 to provide easy transportation of the modular phantom carrier 400 by a human operator. The exterior frame 430 also includes an alignment pin 420, extending outward from the exterior frame 430.

In operation, the modular phantom carrier 400 is slid into an aperture in an x-ray system (not shown) by an operator grasping the handle 410. The aperture in the x-ray system is shaped so as to position the phantom insert aperture 480 in the path of an x-ray beam. The alignment pin 420 fits into a corresponding notch in the x-ray system aperture. The alignment pin 420 is used to assure that the modular phantom carrier 400 is positioned correctly within the aperture of the x-ray system. The alignment pin 420 minimizes rotational motion of the modular phantom carrier 400 and also prevents the modular phantom carrier 400 from being placed in the aperture of the x-ray system incorrectly, for example upside down. Additional positioning tabs may be added to the modular phantom carrier 400 to further minimize its motion.

Within the exterior frame 430 of the modular phantom carrier 400 is an interior mesh 440 which is in the plane of the exterior frame 430 and affixed to the exterior frame 430. The interior mesh 440 is preferably composed of a metal mesh such as steel mesh. The interior mesh 440 is generally circular in aspect. Centered in the interior mesh is the phantom insert aperture 480. The phantom insert aperture 480 is a generally circular aperture and has a ledge 485 running along the inside of the edge of the phantom insert aperture 480. The phantom insert aperture 480 also includes a positioning notch 470.

In operation, a phantom such as the phantom 100 of FIG. 1 is inserted into the phantom insert aperture 480. The edge of the inserted phantom is supported by the ledge 485. Upon insertion, the positioning tab of the inserted phantom fits into the positioning notch 470 to prevent the inserted phantom from rotating inside the phantom insert aperture 480 and to position the phantom correctly.

Preferably, the interior mesh 440 is composed of a steel mesh similar to the upper mesh 290 and lower mesh 295 of the mesh phantom 200 of FIG. 2. Just as the meshes of the mesh phantom 200 provide sites for the determination of the resolution non-uniformity of x-ray system, the interior mesh 440 may provide additional sites. For example, resolution non-uniformity readings may be taken in several locations throughout the interior mesh 440 and then compared to allow a determination of resolution non-uniformity across a greater area. The determination of the resolution non-uniformity across a greater area may be more indicative of the resolution non-uniformity of the system as a whole. The resolution non-uniformity readings taken at locations in the interior mesh 440 may also be compared with resolution non-uniformity readings from the meshes of the mesh phantom 200 of FIG. 2 or the coupon phantom 300 of FIG. 3.

The interior mesh 440 also includes eight casing fasteners 450 positioned generally evenly around the phantom insert aperture 480. The casing fasteners 450 are positioned at a generally constant distance from the each of the phantom insert aperture 480. Three of the casing fasteners 450 are equipped with rotating fasteners 460. The rotating fasteners 460 are preferably composed of plastic tabs. Each rotating fastener 460 rotates around the casing fastener 450 to which the rotating fastener 460 is attached. The rotating fasteners 460 are spaced generally evenly around the phantom insert aperture 480. Although the use of three rotating fasteners is preferred, a great or lesser number of casing fasteners may be used. Additionally, the shape of the rotating fasteners may be varied.

Figure 5:
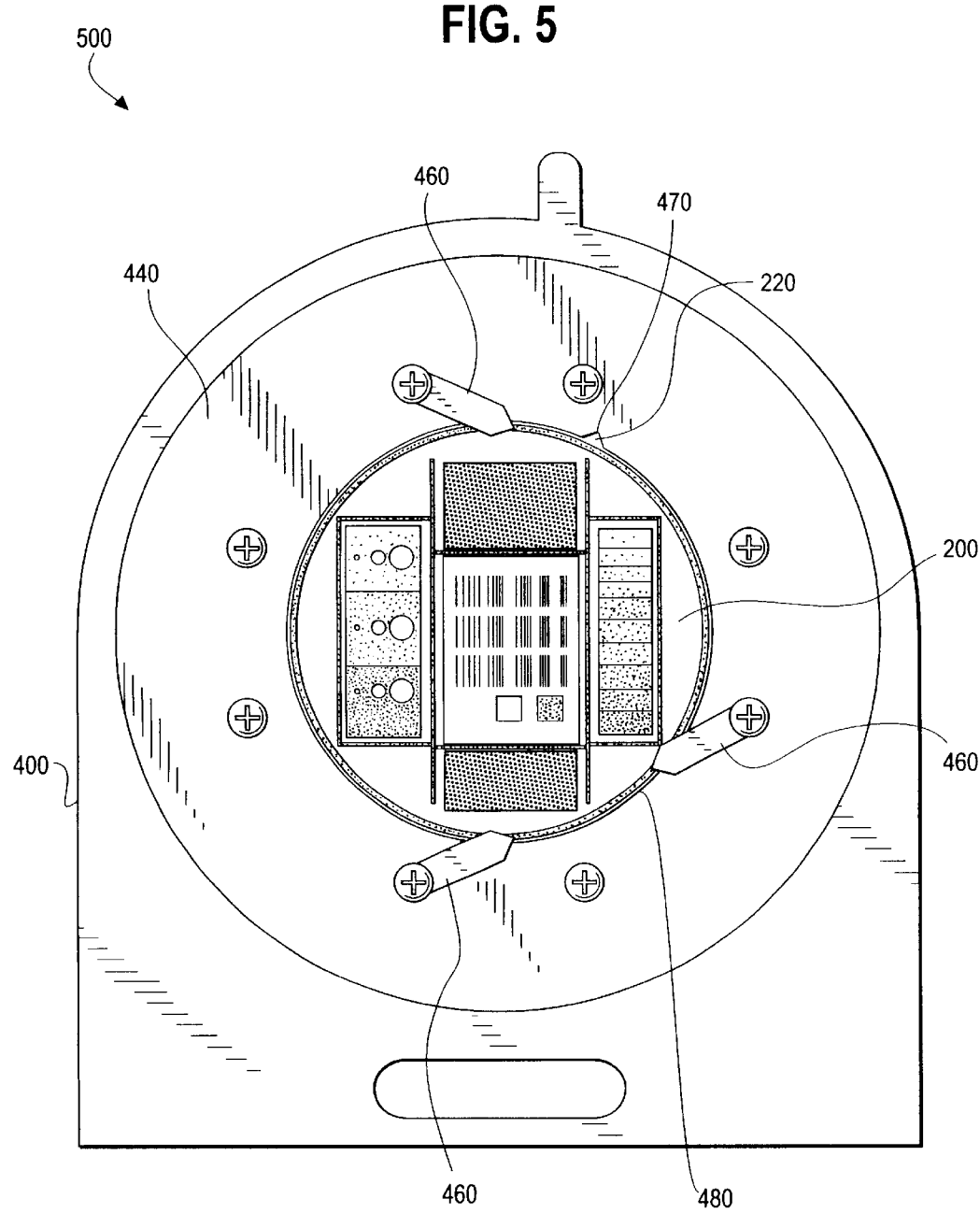
FIG. 5 illustrates a preferred embodiment of the present invention having a phantom-carrier set comprised of the modular phantom carrier of FIG. 4 with the mesh phantom of FIG. 2 installed in the phantom insert aperture of the modular phantom carrier.

FIG. 5 illustrates a preferred embodiment of the present invention having a phantom-carrier set 500 comprised of the modular phantom carrier 400 of FIG. 4 with the mesh phantom 200 of FIG. 2 installed in the phantom insert aperture 480 of the modular phantom carrier 400. Although the mesh phantom 200 of FIG. 4 is used in this example, the phantom 100 of FIG. 1 and the coupon phantom 300 of FIG. 3 may also be used. The positioning tab 220 of the mesh phantom 200 fits into the positioning notch 470 of the of the modular phantom carrier 400 to prevent rotation of the mesh phantom 200 and to prevent the mesh phantom 200 from being inserted incorrectly. Once the mesh phantom 200 has been placed into the phantom insert aperture 480, the rotating fasteners 460 are rotated inward toward the center of the phantom insert aperture 480 to a lock position as shown. Once the rotating fasteners 460 are rotated to the lock position, the rotating fasteners 460 hold the mesh phantom 200 firmly in place and prevent the mesh phantom 200 from being removed from the phantom insert aperture 480.

Figure 6:
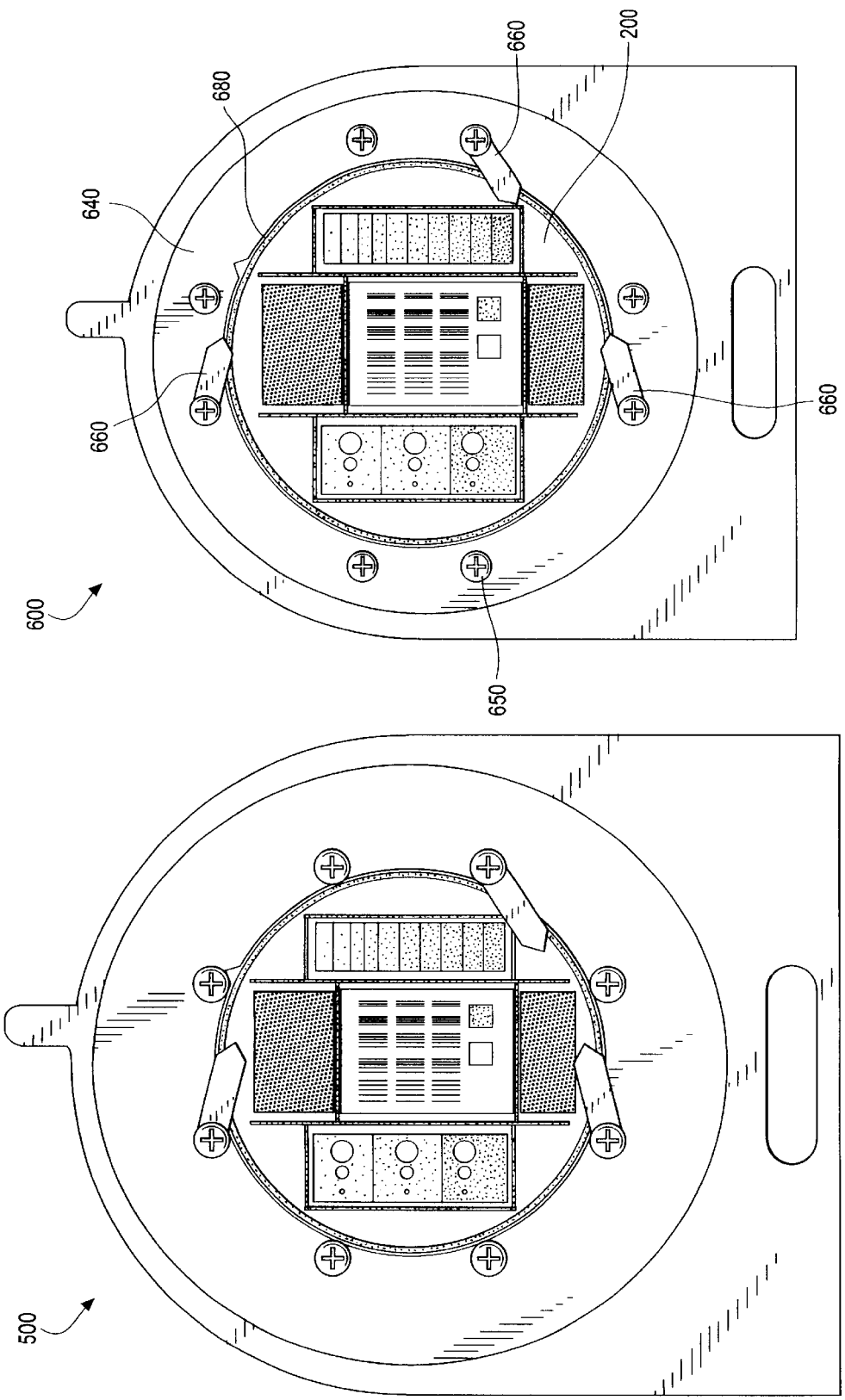
FIG. 6 illustrates a preferred embodiment of the present invention having the phantom-carrier set of FIG. 5 and a reduced aspect phantom-carrier set.

FIG. 6 illustrates a preferred embodiment of the present invention having the phantom-carrier set 500 of FIG. 5 and a reduced aspect phantom-carrier set 600. The reduced aspect phantom-carrier set 600 is generally similar to the phantom-carrier set 500 of FIG. 5 and includes each element of the phantom-carrier set 500 of FIG. 5 including an interior mesh 640, a plurality of casing fasteners 650, a plurality of rotating fasteners 660, and a phantom insert aperture 680. As in the phantom-carrier set 500 of FIG. 5, the mesh phantom 200 has been installed into the phantom insert aperture 680 of the reduced aspect phantom-carrier set 600.

The phantom insert aperture 680 of the reduced aspect phantom-carrier set 600 is the same size as the phantom insert aperture 480 of the phantom-carrier set 500 of FIG. 5. However, because the reduced-aspect phantom-carrier set 600 is smaller than the phantom-carrier 500, the interior mesh 640 of the reduce aspect phantom-carrier set 600 extends outward from the phantom insert aperture 680 only a short distance beyond the casing fasteners 650. The reduced aspect phantom-carrier set 600 functions generally similarly to the phantom-carrier set 500 of FIG. 5, but may be used in smaller x-ray systems. Additionally, the reduced aspect phantom-carrier set 500 may be employed for different sizes of image receptors.

Although the interior mesh 640 of the reduced aspect phantom-carrier set 600 is less in total area than the interior mesh 440 of the phantom-carrier set, the interior mesh 640 may still allow resolution non-uniformity readings to be determined similar to the interior mesh 440. Additionally, although the use of three rotating fasteners 660 is preferred, a greater or lesser number of fasteners or fasteners of different shapes may be used.

Figure 7:
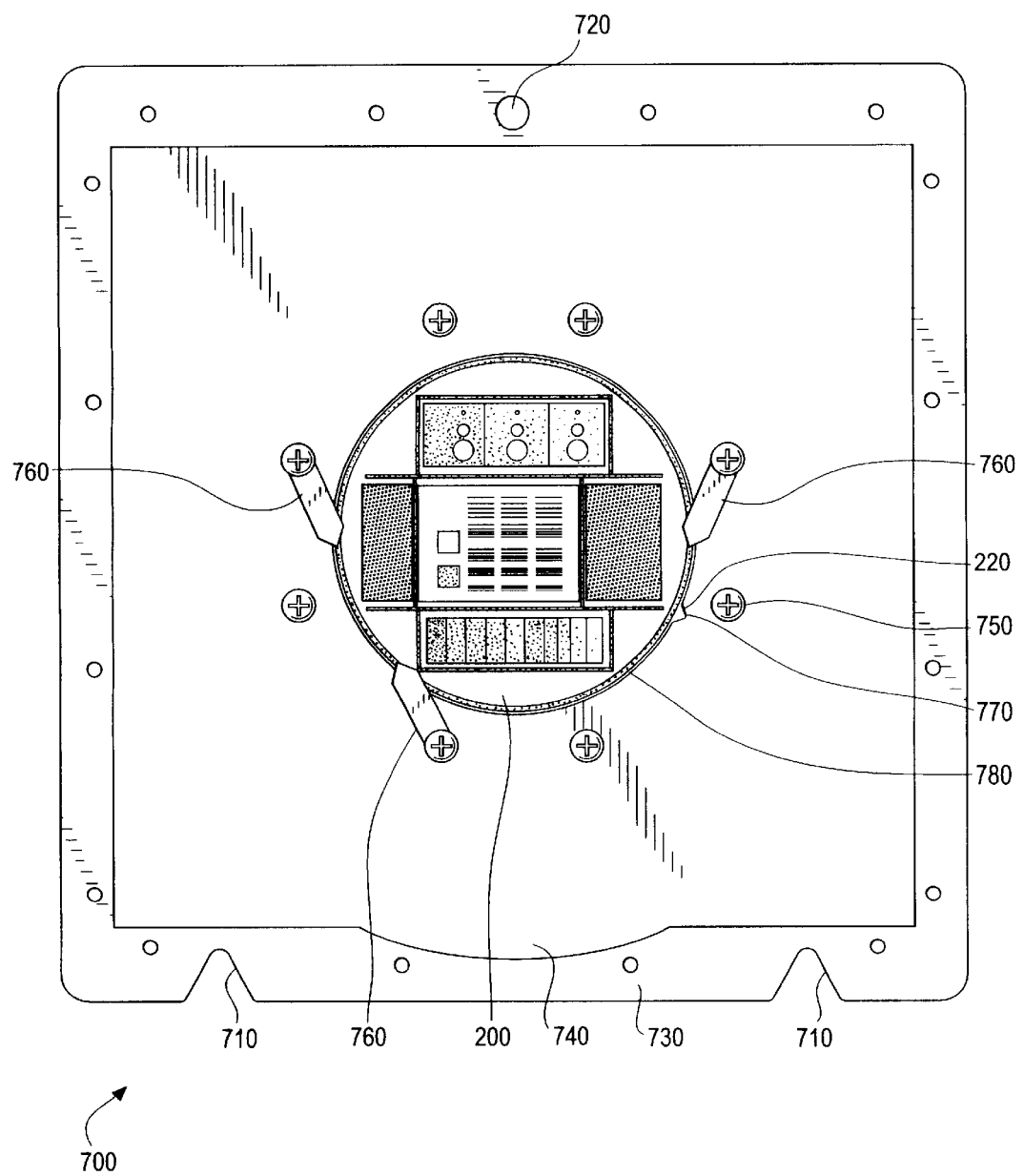
FIG. 7 illustrates a preferred embodiment of the present invention having a square phantom-carrier set.

FIG. 7 illustrates a preferred embodiment of the present invention having a square phantom-carrier set 700. The square phantom-carrier set 700 includes an exterior frame 730, an interior mesh 740, a plurality of casing fasteners 750, a plurality of rotating fasteners 760, a positioning notch 770, and a phantom insert aperture 780. In FIG. 7, the mesh phantom 200 from FIG. 2 has been inserted into the phantom insert aperture 780 of the square phantom-carrier set 700. Similar to the phantom-carrier set 500 of FIG. 5, the positioning tab 220 of the mesh phantom 200 fits into the positioning notch 770. Also, similar to the phantom-carrier set 500 of FIG. 5, the square phantom-installed carrier 700 is generally flat and planar. The square phantom-installed carrier 700 may be used for square x-ray image receptors.

The exterior frame 730 is preferably composed of a study, metallic frame such as an aluminum frame. The exterior frame 730 is generally square in aspect. Within and attached to the exterior frame 730 is the interior mesh 740 which is preferably composed of a steel mesh similar to the interior mesh 440 of the phantom carrier 400 of FIG. 4. Centered in the interior mesh 740 is the phantom insert aperture 780. Surrounding the phantom insert aperture 780 and spaced generally evenly around the phantom insert aperture 780 are the casing fasteners 750. Three of the casing fasteners 750 are equipped with rotating fasteners 760 as in the phantom-carrier set 500 of FIG. 5. The square phantom-carrier set 700 functions generally similarly to the phantom-carrier set 500 of FIG. 5, but may be used in x-ray systems with accepting a square phantom carrier.

Although the interior mesh 740 of the square phantom-carrier set 700 is greater in total area then the interior mesh 440 of the phantom-carrier set, the interior mesh 740 may still allow resolution non-uniformity readings to be determined similar to the interior mesh 440. Additionally, although the use of three rotating fasteners 760 is preferred, a greater or lesser number of fasteners or fasteners of different shapes may be used.

The square phantom-carrier set 700 also includes positioning notches 710 and alignment aperture 720. In operation, the square phantom-carrier set 700 is slid into an x-ray system so that the positioning notches 710 fit into positioning tabs inside the x-ray system. Once the positioning notches 710 have been positioned, a pin on the x-ray system slides through the alignment aperture 720 and locks the square phantom-carrier set 700 to the x-ray system.

Figure 8:
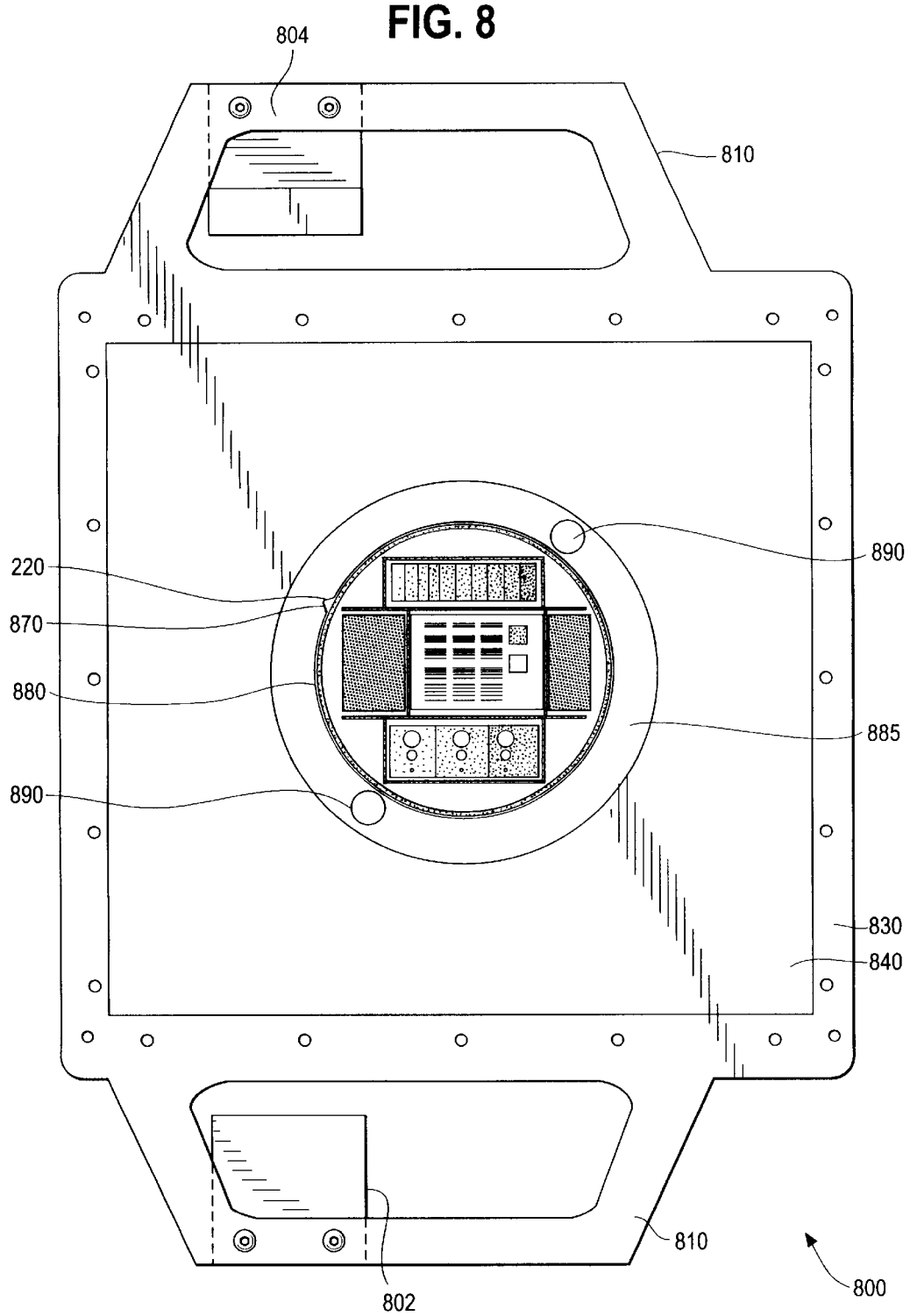
FIG. 8 illustrates a preferred embodiment of the present invention having a two-handled phantom-carrier set.

FIG. 8 illustrates a preferred embodiment of the present invention having a two-handled phantom-carrier set 800. The two-handled phantom-carrier set 800 includes two handles 810, an exterior frame 830, an interior mesh 840, a positioning notch 870, a phantom insert aperture 880, a removable fastening ring 885, and a plurality of fastening pins 890. In FIG. 8, the mesh phantom 200 of FIG. 2 has been inserted into the phantom insert aperture 880 of the two-handled phantom-carrier set 800. Similar to the phantom-carrier set 500 of FIG. 5, the positioning tab 220 of the mesh phantom 200 fits into the positioning notch 870. Also, similar to the phantom-carrier set 500 of FIG. 5, the two-handled phantom-carrier set 800 is generally flat and planar. The exterior frame 830 is preferably composed of a study, metallic frame such as an aluminum frame. The exterior frame 830 is generally square in aspect, but has two handles 810 extending outward on opposite sides of the exterior frame 830.

The two fastening pins 890 are mounted opposite each other in the removable fastening ring 885. The fastening ring 885 and fastening pins 890 are preferably composed of plastic. Each fastening pin 890 extends through the removable fastening ring 885 and engages a fixture (not shown) mounted in the interior mesh 840. In operation, the removable fastening ring 885 with mounted fastening pins 890 is removed and a phantom such as the mesh phantom 200 of FIG. 2 is inserted into the phantom insert aperture 880. The removable fastening ring 885 is replaced and each fastening pin 890 is engaged with a corresponding fixture in the interior mesh 840. Once the fastening pins 890 have been engaged, the removable fastening ring 885 holds the mesh phantom 200 firmly in place and prevents the mesh phantom from being removed from the phantom insert aperture 880. The fastening pins 890 are preferably composed of commercially available Nylatch™ fasteners.

The two-handled phantom-carrier set 800 functions generally similarly to the phantom-carrier set 500 of FIG. 5, but may be used in x-ray systems accepting a two-handled phantom carrier.

The two-handled phantom-carrier set 800 also includes a left mounting bracket 802 and a right mounting bracket 804. The left mounting bracket 802 and right mounting bracket 804 are attached to the handles 810.

Figure 15:
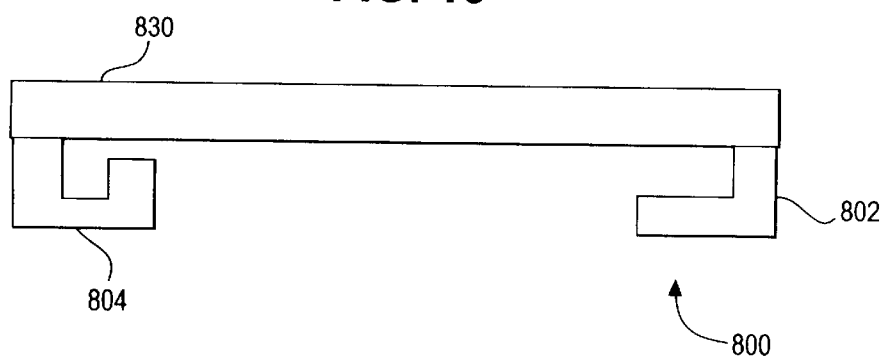
FIG. 15 is a side view of the two-handled phantom-carrier set including the left and right mounting brackets.

FIG. 15 is a side view of the two-handled phantom-carrier set 800 including the left mounting bracket 802 and the right mounting bracket 804. In operation, the mounting brackets 802–804 are positioned on mounting elements on an x-ray system. The two-handled phantom-carrier set 800 may be employed in vertically aligned x-ray systems.

Although the interior mesh 840 of the two-handled phantom-carrier set 800 differs in total area from the interior mesh 440 of the phantom-carrier set, the interior mesh 840 may still allow resolution non-uniformity readings to be determined similar to the interior mesh 440. Additionally, although the use of two fastening pins 890 is preferred, a greater or lesser number of fastening pins or fastening pins of different shapes may be used.

As mentioned above, the use of a phantom carrier to position a phantom in an x-ray system may yield considerable benefits in the calibration of an x-ray system. Among the benefits afforded by the use of a phantom carrier are the repeatable and accurate positioning of a phantom in a known location and orientation. Accurate positioning of a phantom assists in the interpretation of the calibration pattern generated by the phantom. Additionally, accurate positioning becomes increasingly important when multiple measurements are performed on an x-ray system such as when readings are taken with multiple phantoms or when readings are taken at time intervals. Taking readings with multiple phantoms may be desirable because different phantoms may calibrate different parameters or sets of parameters of an x-ray system. Taking readings at time intervals may be desirable to generate trending data of the performance of the x-ray system over time.

Additionally, in each of the modular phantom carriers of FIGS. 4–8, a phantom may be inserted and removed from the carrier. In this fashion, several phantoms or types of phantoms may be used with a single modular phantom carrier. Several embodiments of phantom carriers of different sizes and shapes may be necessary to accommodate specific x-ray systems. However, each phantom carrier accommodates any phantom of a specific size, thus allowing a single phantom to be used with any number of x-ray systems.

The use of a modular phantom carrier with a standard phantom size across x-ray systems allows an owner of multiple x-ray systems to purchase only a single phantom for calibration of all x-ray systems instead of having to purchase a new carrier with an embedded phantom for each x-ray system. Additionally, servicing and maintenance of x-ray system may be simplified because, to be able to test all x-ray systems, only a single, easily transported phantom need be brought to a worksite rather than a multitude of bulky, weighty, carriers with embedded phantoms for each x-ray system.

FIG. 9 illustrates a flowchart 900 for using the modular phantom carrier according to a preferred embodiment of the present invention. First, at step 910, an x-ray phantom is inserted into the modular x-ray carrier of the present invention. In the preferred embodiments above, any of the phantoms (the phantom 100 of FIG. 1, the mesh phantom 200 of FIG. 2 or the coupon phantom 300 of FIG. 3) may be inserted into the phantom insert apertures any of the phantom carriers of FIGS. 4–8. In order to insert any of the phantoms into the phantom insert apertures of any of the carriers, the positioning tab of the phantom is positioned in the notch on the carrier. Next, at step 920, the x-ray phantom is locked to the x-ray carrier. As set forth above, the phantom is preferably locked to the carrier by the use of at least one rotating fastener rotating to a lock position or the use of a plastic ring having at least one locking pin engaging a fixture in said carrier. Next, at step 930, the carrier, including the locked-in phantom, is positioned in an x-ray system. As set forth above, the phantom carriers of FIG. 4–6 have an alignment pin that is inserted into a corresponding notch in said x-ray system. The alignment pin aids in the positioning of the carrier. Finally, at step 940, x-rays are transmitted through the phantom.

While particular elements, embodiments and applications of the present invention have been shown and described, it is understood that the invention is not limited thereto since modifications may be made by those skilled in the art, particularly in light of the foregoing teaching. It is therefore contemplated by the appended claims to cover such modifications and incorporate those features which come within the spirit and scope of the invention.

What is claimed is:

1. An x-ray phantom for use in an x-ray system, said x-ray phantom comprising:
    a base;
    a metallic perimeter ring attached to said base and substantially conforming to a perimeter of said base; and
    at least one sub-phantom attached to said base, for assisting in the determination of at least one performance parameter of said x-ray system.

2. The phantom of claim 1 further including at least one metallic line segment surrounding at least one sub-phantom.

3. The phantom of claim 1 further including a positioning tab located on said base for positioning said base.

4. The phantom of claim 1 further including at least one fiducial for use in determining the location of at least one sub-phantom.

5. The phantom of claim 1 wherein said sub-phantom comprises a step-intensity sub-phantom.

6. The phantom of claim 5 wherein said step-intensity sub-phantom comprises metallic layers of varying thickness.

7. The phantom of claim 1 wherein said sub-phantom comprises a contrast detail sub-phantom.

8. The phantom of claim 7 wherein said contrast detail sub-phantom comprises at least one metallic layer of varying thickness, said metallic layer having at least one aperture.

9. The phantom of claim 1 wherein said sub-phantom comprises a resolution sub-phantom.

10. The phantom of claim 9 wherein said resolution sub-phantom comprises a metallic layer having at least one resolution pattern.

11. The phantom of claim 9 wherein at least one resolution pattern is comprised of at least two apertures in said metallic layer.

12. The phantom of claim 1 wherein said sub-phantom comprises at least one of a high intensity contrast region and a low intensity contrast region.

13. The phantom of claim 1 wherein said sub-phantom comprises a mesh sub-phantom.

14. The phantom of claim 1 wherein said sub-phantom comprises a coupon sub-phantom.

15. An x-ray phantom for use in an x-ray system, said x-ray phantom comprising:
- a base;
- at least one mesh sub-phantom, attached to said base, for assisting in the determination of the resolution non-uniformity of said x-ray system; and
- a metallic feature for use in determining the localization of said mesh sub-phantom.

16. The phantom of claim 15 wherein said mesh sub-phantom is comprised of a metallic layer having apertures at uniform intervals.

17. The phantom of claim 15 wherein said metallic feature is a metallic perimeter ring attached to said base near the perimeter of said base.

18. The phantom of claim 15 wherein said metallic feature is at least one metallic line segment surrounding at least on sub-phantom.

19. The phantom of claim 15 further including a positioning tab located on said base for positioning said base.

20. The phantom of claim 15 wherein said metallic feature is at least one fiducial for use in determining the location of at least one sub-phantom.

21. An x-ray phantom for use in an x-ray system, said x-ray phantom comprising:
- a base; and
- a coupon sub-phantom attached to said base, for assisting in the determination of the horizontal and vertical Modulation Transfer Function (MTF) of said x-ray system.

22. The phantom of claim 21 wherein said coupon sub-phantom comprises at least one metallic sheet.

23. The phantom of claim 22 wherein said at least one metallic sheet is rotated.

24. The phantom of claim 21 further including a metallic perimeter ring attached to said base near the perimeter of said base.

25. The phantom of claim 21 further including at least one metallic line segment surrounding at least one sub-phantom.

26. The phantom of claim 21 further including a positioning tab for positioning said base.

27. The phantom of claim 21 further including at least one fiducial for use in determining the location of at least one sub-phantom.

28. A modular x-ray phantom carrier comprising:
- a frame for insertion into an x-ray system to position an x-ray phantom in an x-ray system; and
- a locking fastener for removeably attaching said x-ray phantom to said frame.

29. The phantom carrier of claim 28 further including at least one alignment pin protruding from said frame for assisting in the positioning of said frame.

30. The phantom carrier of claim 28 wherein said fastener comprises at least one rotating fastener, said rotating fastener rotating to a lock position to attach said x-ray phantom to said frame.

31. The phantom carrier of claim 28 wherein said fastener comprises a ring having at least one fastening pin engaging a fixture in said phantom carrier to attach said x-ray phantom to said frame.

32. The phantom carrier of claim 28 further including a phantom insert aperture for receiving a phantom.

33. The phantom carrier of claim 32 wherein said phantom insert aperture includes at least one notch for receiving a positioning tab on an inserted phantom.

34. The phantom carrier of claim 28 further including an interior mesh for assisting the determination of the resolution non-uniformity of said x-ray system.

35. A method for assisting in the determination of at least one parameter of an x-ray system comprising:
- fastening a first x-ray phantom to an x-ray phantom carrier using a locking fastener, said first x-ray phantom assisting in the determination of at least one parameter of an x-ray system;
- positioning said x-ray phantom carrier in an x-ray system; and
- transmitting x-rays through said first x-ray phantom.

36. The method of claim 35 further comprising:
- substituting a second x-ray phantom into said x-ray phantom carrier in place of said first x-ray phantom, said second x-ray phantom assisting in the determination of at least one parameter of said x-ray system;
- positioning said x-ray phantom carrier in said x-ray system; and
- transmitting x-rays through said second x-ray phantom.

37. The method of claim 35 wherein said fastening step further includes inserting said first x-ray phantom into a phantom insert aperture in said x-ray phantom carrier.

38. The method of claim 37 wherein said fastening step further includes inserting at least one positioning tab on said first x-ray phantom into at least one notch on said x-ray phantom carrier.

39. The method of claim 35 wherein said fastening step comprises the step of rotating a rotating fastener to a lock position.

40. The method of claim 35 wherein said fastening step comprises the step of positioning a ring having at least one fastening pin over said first x-ray phantom and engaging a fixture in said x-ray phantom carrier with said at least one fastening pin.

41. The method of claim 35 wherein said positioning step further comprises the step of inserting an alignment pin on said x-ray phantom carrier into a corresponding notch in said x-ray system.

42. An x-ray phantom for use in an x-ray system, said x-ray phantom comprising:
- a base; and
- a metallic perimeter ring attached to said base and substantially conforming to a perimeter of said base.

43. An x-ray phantom for use in an x-ray system, said x-ray phantom comprising:
- a base; and
- at least one metallic line segment surrounding at least one sub-phantom.

44. A modular x-ray phantom carrier including:
- a rotating fastener, said rotating fastener rotating to a lock position to attach an x-ray phantom to said x-ray phantom carrier.

45. A modular x-ray phantom carrier including:
- a phantom insert aperture including at least one notch for receiving a positioning tab on an inserted phantom.

46. An x-ray phantom for use in an x-ray system, said x-ray phantom comprising:
- a base; and
- at least one positioning tab that extends from said base.

* * * * *